US00PP32025P2

(12) United States Plant Patent
Hansen

(10) Patent No.: US PP32,025 P2
(45) Date of Patent: Jul. 28, 2020

(54) ***PHLOX* PLANT NAMED 'BABY DOLL PINK'**

(50) Latin Name: ***Phlox* hybrid**
Varietal Denomination: Baby Doll Pink

(71) Applicant: Hans A Hansen, Zeeland, MI (US)

(72) Inventor: Hans A Hansen, Zeeland, MI (US)

(73) Assignee: Walters Gardens, Inc., Zeeland, MI (US)

( * ) Notice: Subject to any disclaimer, the term of this patent is extended or adjusted under 35 U.S.C. 154(b) by 0 days.

(21) Appl. No.: 16/501,955

(22) Filed: Jul. 10, 2019

(51) Int. Cl.
*A01H 5/02* (2018.01)
*A01H 6/70* (2018.01)

(52) U.S. Cl.
USPC ..... Plt./320
CPC ..... *A01H 6/70* (2018.05)

(58) Field of Classification Search
USPC ..... Plt./320
CPC ..... A01H 6/70
See application file for complete search history.

*Primary Examiner* — Anne Marie Grunberg

(57) ABSTRACT

A new and unique cultivar of garden *phlox* named *Phlox* 'Baby Doll Pink' multi-stemmed, very short, upright, slowly-spreading habit with clean, medium-green, glossy, lanceolate leaves with exceptional powdery mildew resistance. Foliage is thick with stiff stems. Flowers are medium pink with white eye zone markings produced on branched peduncles and nearly cover the top of the plant beginning early summer, about two weeks prior typical *Phlox paniculata* cultivars and continuing for about six weeks. 'Baby Doll Pink' is especially suitable as a potted plant, for the garden, for attracting hummingbirds and butterflies, and for cut flower arrangements.

1 Drawing Sheet

Botanical classification: *Phlox* hybrid.
Variety denomination: 'Baby Doll Pink'.

STATEMENT REGARDING PRIOR DISCLOSURES UNDER 37 CFR 1.77(B)(6)

The first disclosure, in the form of a sale, was made by Walters Gardens, Inc. on Jul. 16, 2018 to Sheridan Nurseries. Subsequently, Walters Gardens, Inc. also sold the new plant to Willoway Nurseries, Inc. on Aug. 8, 2018, to Prides Corner Farms on Aug. 13, 2018 and to Overdevest Nurseries, L.P. on Aug. 20, 2018. Walters Gardens, Inc. obtained the new plant and all information relating thereto, from the inventor. No plants of *Phlox* 'Baby Doll Pink' have been sold, in this country or anywhere in the world, nor has any disclosure of the new plant been made, more than one year prior the filing date of this application, and such sale or disclosure within one year was either derived directly or indirectly from the inventor.

BACKGROUND OF THE INVENTION

The present invention relates to a new and distinct cultivar of *Phlox* plant, known as *Phlox* 'Baby Doll Pink' and will be referred to hereafter by its cultivar name or the "new plant". The new plant was the result of an insect pollination in an isolation block of a proprietary, unreleased, unnamed hybrid identified by the breeder code 13-496-1 and a sibling of 13-496-1. The exact male parent is unknown. The female parent was grown in trial isolation block at a wholesale perennial nursery in Zeeland, Mich., and seed was collected in the fall of 2014. During the trial process the new plant was identified by the breeder code 14-663-1. 'Baby Doll Pink' has been asexually propagated by tip and basal stem cuttings in the greenhouses at the same nursery in Zeeland, Mich. since 2016. The unique characteristics of the new plant have been found to be reproducible and stable in successive generations of asexually propagated plants and the resultant plants have been found to be identical to the original selection.

BRIEF SUMMARY OF THE PLANT

*Phlox* 'Baby Doll Pink' is unique from its parents and all other tall garden *phlox* or other hybrid *Phlox* known to the inventor. The new plant differs from the female parent in that the female parent is taller and has different colored flowers. Comparison with the male parent is not possible. The most closely comparison cultivars known to the inventor are *Phlox* 'Cloudburst' U.S. Plant Pat. No. 30,289, 'Kung Fuchsia' U.S. Plant patent application Ser. No. 16/501,030, 'Opening Act Blush' U.S. Plant Pat. No. 27,462, 'Forever Pink' U.S. Plant Pat. No. 24,918, 'Fashionably Early Flamingo' U.S. Plant Pat. No. 29,911 and 'Fashionably Early Princess' U.S. Plant Pat. No. 28,680. 'Cloudburst' is much taller in habit and has more lavender purple flowers with bright pink eyes. 'Kung Fuchsia' is taller in habit, thicker foliage and has flowers that are bright fuchsia with a light pink eye zone. 'Opening Act Blush' has a slightly taller habit with smaller, light lavender-pink flowers. 'Forever Pink' has a shorter flower season smaller, darker pink flowers without the white eye, and the habit is taller. 'Fashionably Early Flamingo' has taller and broader habit with larger foliage and larger inflorescence and the flower lacks the white eye. 'Fashionably Early Princess' has fragrant flowers of light fuchsia-pink with a darker eye on taller plants. 'Amethyst Pearl' U.S. Plant Pat. No. 28,487 has light amethyst-pink flowers and taller habit. 'Minnie Pearl' (not patented) has white flowers and taller habit. 'Lil' Cahaba' (not patented) has a taller habit with pinky mauve flowers. 'David's Lavender' U.S. Plant Pat. No. 17,793 is taller with lavender flowers. 'Baby Doll Pink' differs from all other *phlox* known to the inventor in the following repeatedly observed traits in combination:

1. Plants of short upright habit, slowly spreading by short rhizomes, producing clean, glossy, medium-green, lanceolate leaves;
2. Showing exceptional powdery mildew resistance;
3. Multiple branched, stems produce rounded mounds of flowers starting early in the season;
4. Flower on strong stiff stems of about 28.0 cm tall producing medium pink flower faces with small white eye zones;
5. Flowers cover nearly the entire top of the plant;
6. Flowering beginning in early-summer about two weeks prior to typical *Phlox paniculata* cultivars and re-blooming through late-summer.

BRIEF DESCRIPTION OF THE DRAWINGS

The photographs of the new plant demonstrate the unique traits of 'Baby Doll Pink' and the overall appearance of the plant at two-years-old grown in a full sun trial garden in Zeeland, Mich. The colors are as accurate as reasonably possible with color reproductions. Variation in ambient light spectrum, source and direction may cause the appearance of minor variation in color.

DETAILED BOTANICAL DESCRIPTION

Figure 1:
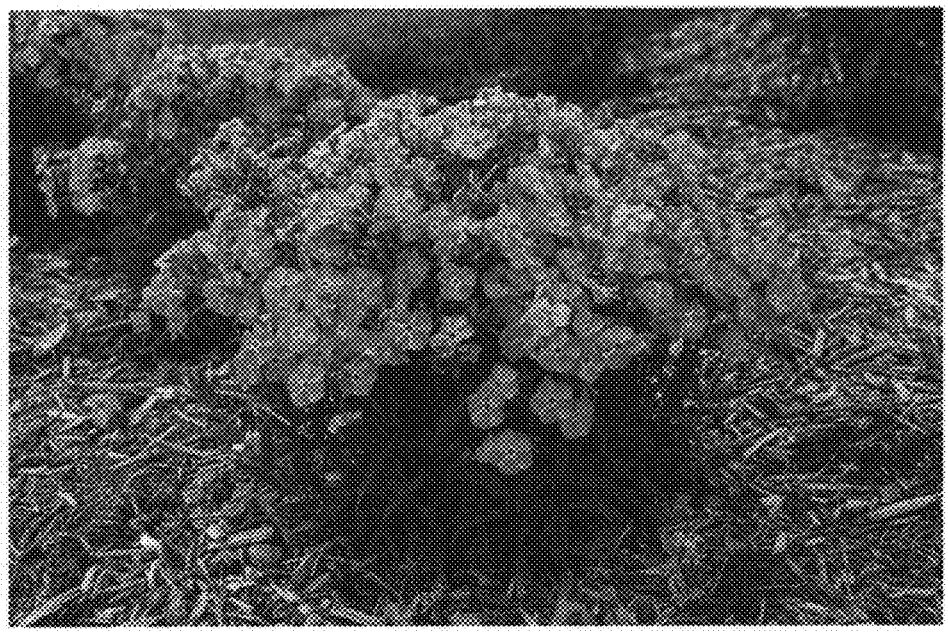
FIG. 1 shows the new plant in peak flower in the landscape.
Figure 2:
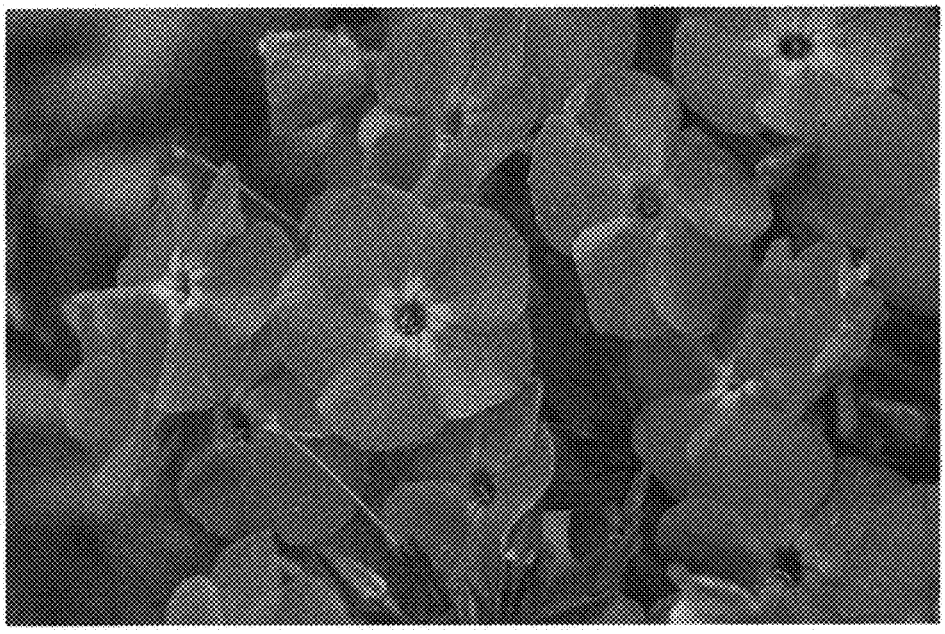
FIG. 2 shows a close-up of the floriferous flower head with flowers and buds.

The following descriptions and color references are based on the 2015 edition of The Royal Horticultural Society Colour Chart except where common dictionary terms are used. *Phlox* 'Baby Doll Pink' has not been observed under all possible environments. The phenotype may vary slightly with different growing environments such as temperature, light, fertility, soil pH, moisture and maturity levels, but without any change in the genotype. The following observations and size descriptions are based on two-year-old plants in the full sun trial garden of a wholesale perennial nursery in Zeeland, Mich. with supplemental fertilizer and water as needed.

Botanical classification: *Phlox* hybrid;

Parentage: Female or seed parent an unnamed, unreleased proprietary hybrid assigned the breeder code 13-496-1 with ancestry comprising *Phlox carolina* 'Lil' Cahaba', 'Minnie Pearl' and 'David's Lavender'; male or pollen parent unknown sibling of 13-496-1;

Plant habit: Hardy herbaceous perennial, densely upright, producing about 40 rigid upright stems; flowering about 30.0 cm tall and about 43.0 cm wide; flowering begins early summer in Michigan and continuing for about 5 weeks;

Propagation: Stem cuttings; rooting in about 14 days;

Time to produce finished crop in 3.8 liter pots: About 8 to 10 weeks; moderate rate of growth;

Root: Primary roots to about 1.0 mm thick; secondary fibrous and freely branching; color creamy white to tan depending on soil type;

Leaves: Simple, opposite, lanceolate; entire margin on mature leaves, young expanding leaves micro-ciliolate; narrowly acute apex; rounded to attenuate base;

Leaf size: To about 88.0 mm long by about 20.0 mm wide, average about 65.0 mm long by about 10.0 mm wide;

Leaf surfaces: Glabrous and lustrous abaxial and adaxial;

Leaf color expanding: Abaxial nearest RHS 146D, adaxial nearest RHS 144A;

Leaf color at flowering: Abaxial nearest RHS 146B, adaxial nearest RHS 137B;

Foliage fragrance: None detected;

Veins: Pinnate; glabrous abaxial and adaxial; midrib about 1.0 mm wide at base, slightly sunken adaxial and raised abaxial;

Vein color: Abaxial midrib nearest RHS 146D, adaxial midrib nearest RHS 145A proximally and distally nearest RHS 137B; secondary adaxial and abaxial veins same color as surrounding leaf;

Petiole: Leaves sessile;

Stems: About 40 per plant; terete; stiff; wiry; strong; upright; glabrous; to about 28.0 cm, average about 26.0 cm long and 4.0 mm diameter at base;

Stem color: Nearest RHS 145A;

Nodes: About six per stem below flowers; average internode length about 7.6 cm;

Node color: Nearest RHS 145A;

Inflorescence: A loosely-branched compound corymb of about 40 flowers; flowering portion about 8.0 cm long and 8.0 cm across;

Flowers: Perfect; salverform with flat face and long fused tube; actinomophic; typically with five petals; about 29.0 mm long total with tube about 28.0 mm long; face about 31.0 mm across; attitude upright to slightly outward; self-cleaning;

Flower longevity: Individually about 5 days on plant or as cut flower;

Flower fragrance: None detected;

Buds one to two days prior to opening: Narrowly oblanceolate, to nearly clavate; acute apex with petals twisted about each other; base fused; about 27.0 mm long and 3.0 mm diameter in tube and swollen to 5.0 mm diameter toward apex of convolute petals;

Bud color: Petals variable with nearest both RHS N81B and RHS N80C in tube and bulb;

Petals: Five; margin entire; apex rounded; base fused into tube; abaxial and adaxial limb glabrous, abaxial tube surface glabrous, adaxial tube glabrous except pubescent in region about 2.0 mm to 4.0 mm from base; limbs imbricate about 25 percent over the next petal;

Petal size: Limb to about 14.0 mm wide and about 15.0 mm long, corolla tube to about 28.0 mm long and 2.5 mm diameter a face;

Petal color: (Young) adaxial limb nearest RHS NN74A, center eye nearest RHS 155D (extending 1.0 mm from throat; abaxial limb mottled nearest RHS N74D and lighter than RHS 69D; abaxial tube striated longitudinally nearest RHS 77A & RHS 77D; adaxial corolla tube nearest RHS N81B with basal 5.0 mm of abaxial and adaxial corolla tube nearest RHS 157D;

Petal color: (Mature) adaxial limb nearest RHS 73A, center eye between RHS N187D and RHS N155A (extending 1.0 mm from throat; abaxial limb mottled nearest RHS 76C and nearest RHS 75D; abaxial corolla tube striated longitudinally nearest RHS N81B & RHS 75B; adaxial throat nearest RHS N81B with basal 5.0 mm of abaxial and adaxial corolla tube nearest RHS 157D;

Androecium: Five;

*Filaments*.—Typically five; adnate to adaxial corolla tube except free in terminal 1.0 mm; varying lengths between 18.0 mm and 24.0 mm, less than 0.5 mm in diameter; white, nearest RHS NN155D.

*Anther*.—Five; oblong elliptic; basifixed; longitudinal; about 3.0 mm long by 1.0 mm wide; color nearest RHS 13A.

*Pollen*.—Abundant; color nearest RHS 12A.

Gynoecium: One pistil per flower; to about 26.0 mm long;

*Style*.—Terete; about 22.5 mm long and about 0.2 mm diameter; color nearest RHS 2D.

*Stigma*.—Trifurcate in the distal 2.0 mm, less than 0.25 mm in diameter; persistent after flower abscission; color nearest RHS 4B.

*Ovary*.—Superior; conical; acute apex, base truncate; about 1.5 mm long and 1.0 mm diameter; color nearest RHS 144A.

Calyx: Tubular; to about 9.0 mm long and 3.0 mm wide at apex;

Sepals: Five; lanceolate; narrowly acute apex, margin entire; base fused; abaxial surface matte and adaxial slightly lustrous; individually about 9.0 mm long and 1.5 mm wide; fused in basal 6.0 mm;

Sepal color: Abaxial variable, nearest RHS 138B, RHS N77B and RHS 187B with margins between RHS NN78B and RHS N77B; adaxial nearest RHS 147B with margins between RHS NN78B and RHS N7&B;

Peduncle: Glabrous, stiff, strong, moderately lustrous, upright, cylindrical; about 28.0 cm long and 2.5 mm diameter at base of flower branches and about 4.0 mm diameter near soil; branches to about 20.0 mm long and 1.0 mm diameter at base;

Peduncle color: Nearest RHS 145A;

Pedicel: Cylindrical; micro-glandular; to about 3.0 mm long and 1.0 mm diameter;

Pedicel color: Nearest RHS 138A;

Fruit and seeds have not yet been observed.

Hardiness and culture: The new plant grows best with plenty of moisture and adequate drainage; hardy to at least from USDA zone 4 through 8.

Disease and pest resistance: *Phlox* 'Baby Doll Pink' demonstrated the excellent powdery mildew resistance caused by *Erysiphe cichoracearum* under conditions of intense pressure that would normally show symptoms.

I claim:

1. A new and distinct cultivar of hybrid *phlox* plant named *Phlox* 'Baby Doll Pink', as herein described and illustrated.

* * * * *